(12) United States Patent
Ludvig

(10) Patent No.: US 9,033,152 B2
(45) Date of Patent: May 19, 2015

(54) STERILIZABLE POUCH

(75) Inventor: Jason Randall Ludvig, Hampstead (CA)

(73) Assignee: AR MEDICOM INC., Lachine, Quebec (CA)

( * ) Notice: Subject to any disclaimer, the term of this patent is extended or adjusted under 35 U.S.C. 154(b) by 0 days.

(21) Appl. No.: 13/391,219

(22) PCT Filed: Aug. 18, 2010

(86) PCT No.: PCT/CA2010/001270
§ 371 (c)(1),
(2), (4) Date: May 2, 2012

(87) PCT Pub. No.: WO2011/020185
PCT Pub. Date: Feb. 24, 2011

(65) Prior Publication Data
US 2012/0205269 A1    Aug. 16, 2012

Related U.S. Application Data

(60) Provisional application No. 61/235,461, filed on Aug. 20, 2009.

(51) Int. Cl.
*A61B 19/02*     (2006.01)
*A61L 2/00*      (2006.01)
*A61B 17/3201*   (2006.01)

(52) U.S. Cl.
CPC .......... *A61B 19/026* (2013.01); *A61B 17/3201* (2013.01); *A61B 2019/0267* (2013.01); *A61L 2/00* (2013.01); *A61L 2202/181* (2013.01); *A61L 2202/24* (2013.01)

(58) Field of Classification Search
USPC .......... 206/459.1, 439, 438, 363, 370, 484.1, 206/484; 422/27, 26
See application file for complete search history.

(56) References Cited

U.S. PATENT DOCUMENTS

| | | | | |
|---|---|---|---|---|
| 3,460,742 A | * | 8/1969 | Langdon ....................... | 206/439 |
| 3,892,314 A | * | 7/1975 | Semp ............................ | 206/363 |
| 3,991,881 A | * | 11/1976 | Augurt ......................... | 206/439 |
| 4,068,757 A | * | 1/1978 | Casey ........................... | 206/363 |
| 4,091,921 A | * | 5/1978 | Lewis ........................... | 206/363 |
| 4,121,714 A | * | 10/1978 | Daly et al. .................... | 206/363 |

(Continued)

FOREIGN PATENT DOCUMENTS

JP    2008-094401    4/2008

OTHER PUBLICATIONS

International Standard ISO 11140-1, Reference No. ISO 11140-1:2005(E), "Sterilization of Health Care Products—Chemical Indicators—Part 1: General requirements", pp. 1-27.

(Continued)

*Primary Examiner* — Steven A. Reynolds
(74) *Attorney, Agent, or Firm* — Pearl Cohen Zedek Latzer Baratz LLP

(57) ABSTRACT

A sterilizable pouch for surgical instruments includes a sterilant permeable sheet with a first sealing strip and a sterilant impermeable sheet with a second sealing strip. The sealing strips are sealed together to define the pouch. At least one sealable open portion is for sealing the pouch after surgical instruments are located inside the pouch. An indicator material for indicating sterile processing conditions inside the pouch is located on an inner surface of the sterilant impermeable sheet inside the pouch.

28 Claims, 10 Drawing Sheets

(56) References Cited

U.S. PATENT DOCUMENTS

| | | | | |
|---|---|---|---|---|
| 4,168,779 | A * | 9/1979 | Yokokoji et al. | 206/439 |
| 4,194,622 | A * | 3/1980 | Lewis | 206/363 |
| 4,206,844 | A * | 6/1980 | Thukamoto et al. | 206/439 |
| 4,358,015 | A * | 11/1982 | Hirsch | 206/439 |
| 4,495,291 | A | 1/1985 | Lawton | |
| 4,660,721 | A * | 4/1987 | Mykleby | 206/439 |
| 5,344,017 | A * | 9/1994 | Wittrock | 206/459.1 |
| 5,590,777 | A * | 1/1997 | Weiss et al. | 206/439 |
| 5,692,610 | A * | 12/1997 | Porteous | 206/388 |
| 5,715,943 | A * | 2/1998 | Thompson, Jr. | 206/363 |
| 5,727,270 | A * | 3/1998 | Cope et al. | 5/710 |
| 5,922,428 | A * | 7/1999 | Pufahl | 428/42.1 |
| 6,251,489 | B1 * | 6/2001 | Weiss et al. | 428/35.2 |
| 6,594,971 | B1 * | 7/2003 | Addy et al. | 53/413 |
| 6,767,509 | B1 * | 7/2004 | Griesbach et al. | 422/29 |
| 6,969,197 | B2 * | 11/2005 | Sedley | 383/200 |
| 7,866,468 | B2 * | 1/2011 | Kyritsis | 206/363 |
| 7,906,070 | B2 * | 3/2011 | Stecklein et al. | 422/28 |
| 7,931,142 | B2 * | 4/2011 | Kyritsis | 206/363 |
| 2001/0023001 | A1 * | 9/2001 | Weiss et al. | 428/35.2 |
| 2005/0092636 | A1 * | 5/2005 | Su-Syin | 206/363 |
| 2005/0189252 | A1 * | 9/2005 | Naylor et al. | 206/439 |
| 2007/0023309 | A1 * | 2/2007 | Davis | 206/438 |
| 2009/0053103 | A1 * | 2/2009 | Mortimer et al. | 422/28 |
| 2009/0123332 | A1 | 5/2009 | Whitehead et al. | |
| 2010/0108551 | A1 * | 5/2010 | Kuo et al. | 206/363 |

OTHER PUBLICATIONS

International Search Report for International Application No. PCT/CA2010/001270 mailed Dec. 2, 2010.

* cited by examiner

STERILIZABLE POUCH

CROSS-REFERENCE TO RELATED APPLICATIONS

This application is a National Phase Application of PCT International Application No. PCT/CA2010/001270, entitled "STERILIZABLE POUCH", International Filing Date Aug. 18, 2010, published on Feb. 24, 2011 as International Publication No. WO 2011/020185, which in turn claims priority from U.S. Provisional Patent Application No. 61/235,461, filed on Aug. 20, 2009, both of which are incorporated herein by reference in their entirety.

TECHNICAL FIELD

The present relates to the sterilization and storage of surgical instruments and more particularly to a sterilizable pouch having a sterilization indicator.

BACKGROUND

Packages or pouches are routinely used to contain sterilized surgical instruments such as those used in medical, dental and veterinary applications. The instruments are located inside the pouch and then sterilized using a variety of sterilants such as ethylene oxide, steam and the like. This simple approach has a number of shortcomings, one of which is the ability to monitor the sterilization conditions inside the pouch to which the instruments are exposed. A number of designs exist which are directed towards this problem. For example, in published US patent application, application number US2009/0123332A1, a package is disclosed in two indicators are located inside the pouch. The indicators are formed by ink printed on a porous paper layer. One of the indicators is located behind a barrier, which prevents contamination of the pouch contents with the ink and also allows the internal indicators to be used in the same compartment as the contents to be sterilized. However, a gap on either side of the barrier would appear to allow the ink to diffuse into the pouch, which in turn may contaminate the surgical instruments.

U.S. Pat. No. 5,344,017 which discloses a pouch having seal lines that are constructed to enclose an indicator at the tapered end of a perimetrical seal. The seal lines extend at right angles to the tapered portions of the perimetrical seal to form a diamond shaped enclosure. In this case, the indicator is located within the diamond shaped enclosure.

Disadvantageously, the major shortcomings of the above designs are that the paper layer on which the indicators are printed is porous and allows steam/ethylene oxide to penetrate the pouch from the surrounding sterilization chamber. Thus, the indicators will change colour when the sterilant comes into contact with the exterior of the pouch and therefore does not provide any added value.

Features of the discovery will be apparent from review of the disclosure, drawings and description below.

BRIEF SUMMARY

We have designed a pouch in which the indicator is located on the film side of the pouch so that the sterilant, such as steam or ethylene oxide, must first pass through the paper and fill the pouch before the indicator changes colour, thereby providing a true indication of the conditions inside the pouch.

According to one aspect, there is provided a sterilizable pouch for surgical instruments, the pouch comprising:
a first sterilant permeable sheet having a first sealing strip;
a sterilant impermeable sheet sealed having a second sealing strip, the first sealing strip being sealed to the second sealing strip to define the pouch, and at least one sealable open portion for sealing the pouch after surgical instruments are located inside the pouch; and
an indicator material for indicating sterile processing conditions inside the pouch, the indicator material being located on an inner surface of the sterilant impermeable sheet inside the pouch.

In one example, the sterilant impermeable sheet is a laminate, which laminate includes a polyethylene sheet and a polypropylene sheet, the polypropylene sheet facing inside the pouch. The indicator material is located on the inner surface of the polypropylene sheet facing the inside of the pouch.

In another example, a second sterilant permeable sheet is located over the indicator material so as to sandwich the indicator material between the polypropylene sheet and the second sterilant permeable sheet. The second sterilant permeable sheet is a strip, the strip extending across substantially the entire width of the pouch.

In another example, the second sterilant permeable sheet is a sheet which covers substantially all of the inner surface of the polypropylene sheet. The sterilant permeable material sheet includes a third sealing strip sealed to the first and second sealing strips and sandwiched therebetween.

In another example, the indicator material is sandwiched between the polypropylene sheet and the polyethylene sheet, the polypropylene sheet having a sterilant permeable area located adjacent the indicator material. The sterilant permeable area is a portion of the polypropylene material which is permeable to sterilant. The indicator material is a chip or a sensor According to another aspect, there is provided a sterilization indicator for use with a sterilizable pouch having a first sterilant permeable sheet and a sterilant impermeable sheet sealed together along a portion of a peripheral area to define the pouch and at least one sealable open portion for sealing the pouch after surgical instruments are located inside the pouch, the sterilization indicator comprising:
an indicator material for indicating sterile processing conditions inside the pouch, the indicator material being located on an inner surface of either of the first sterilant permeable sheet or the imsterilant permeable sheet inside the pouch; and
a layer of sterilant permeable material located over the indicator material to sandwich the indicator material between the layer of sterilant permeable material and the inner surface of either of the first sterilant permeable sheet or the sterilant impermeable sheet, the layer of sterilant permeable material being sealed around the indicator material.

In one example, the layer of sterilant permeable material is sealed to the inner surface of the first sterilant permeable sheet or the sterilant impermeable sheet to cover the indicator material. The layer of sterilant permeable material is sealed along its periphery to the inner surface of the first sterilant permeable sheet or the sterilant impermeable sheet to define a discrete indicator area.

In another example, the layer of sterilant permeable material is a strip of sterilant permeable material. The layer of sterilant permeable material is a sheet of sterilant permeable material which covers substantially all of the inner surface of the first sterilant permeable sheet or the sterilant impermeable sheet. The sterilant permeable material is sealed along a peripheral area together with the first sterilant permeable sheet or the sterilant impermeable sheet. The sterilization indicator is an ink dot. The sterilization indicator is an ink strip. The sterilization indicator is a chip or a sensor.

Accordingly in another aspect, there is provided a sterilizable pouch for surgical instruments, the pouch comprising:

a first sterilant permeable sheet and a sterilant permeable sheet sealed together along a portion of a peripheral area to define the pouch and at least one sealable open portion for sealing the pouch after surgical instruments are located inside the pouch;

an indicator material for indicating sterile processing conditions inside the pouch, the indicator material being located on an inner surface of either the first sterilant permeable sheet or the sterilant permeable sheet inside the pouch; and a layer of sterilant permeable material located over the indicator material to sandwich the indicator material between the layer of sterilant permeable material and the inner surface of either of the first sterilant permeable sheet or the sterilant permeable sheet, the layer of sterilant permeable material being sealed around the indicator material.

In one example, the layer of sterilant permeable material is sealed to the inner surface of the first sterilant permeable sheet or the sterilant impermeable sheet to cover the indicator material. The layer of sterilant permeable material is sealed along its periphery to the inner surface of the first sterilant permeable sheet or the sterilant impermeable sheet to define a discrete indicator area. The layer of sterilant permeable material is a strip of sterilant permeable material.

In another example, the layer of sterilant permeable material is a sheet of sterilant permeable material which covers substantially all of the inner surface of the first sterilant permeable sheet or the sterilant permeable sheet. The sterilant permeable material is sealed along a peripheral area together with the first sterilant permeable sheet or the sterilant impermeable sheet. The sterilization indicator is an ink dot. The sterilization indicator is an ink strip. The sterilization indicator is a chip or a sensor.

In one example, the pouch or the sterilization indicator, as described above, in which the indicator material is a Class 1, Class 2, Class 3, Class 4, Class 5 or Class 6 indicator as defined by International Standard ISO 11140-1.

In one example, the pouch or the sterilization indicator, as described above, in which the indicator material is reactive to one or more sterilants selected from steam, dry heat, irradiation, ethylene oxide, steam-formaldehyde, or vapourized hydrogen peroxide, ozone, HCFC, paracetic acid, dielectric barrier discharge (DBD) plasma or gliding arc (GA) plasma.

BRIEF DESCRIPTION OF THE FIGURES

In order that the herein described may be readily understood, embodiments are illustrated by way of example in the accompanying Figures.

DETAILED DESCRIPTION

In the following description of the embodiments, references to the accompanying drawings are by way of illustration of an example by which the discovery may be practiced. It will be understood that other embodiments may be made without departing from the scope of the discovery disclosed.

Figure 1:
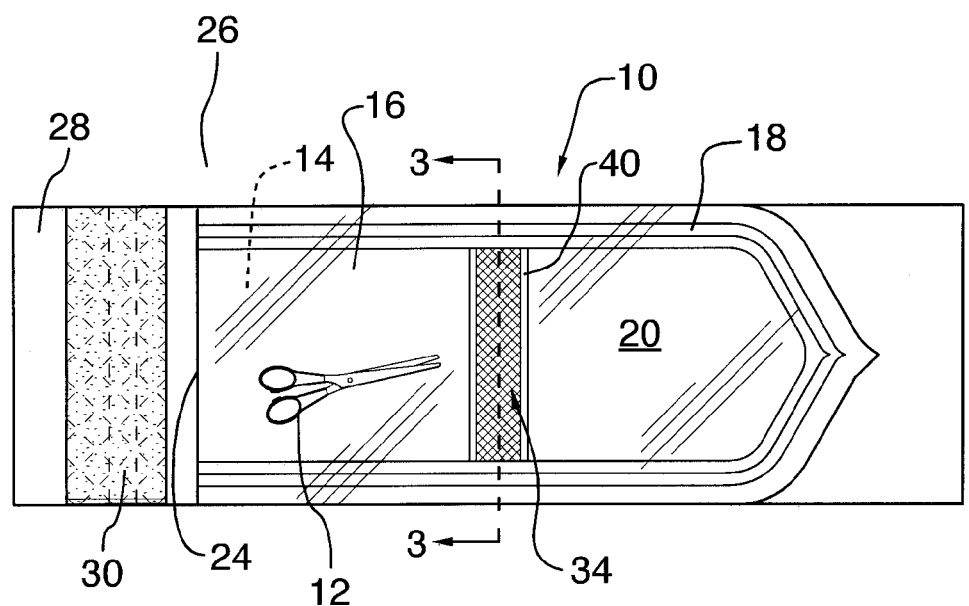
FIG. 1 is a top view of a sterilization pouch.
Figure 2:
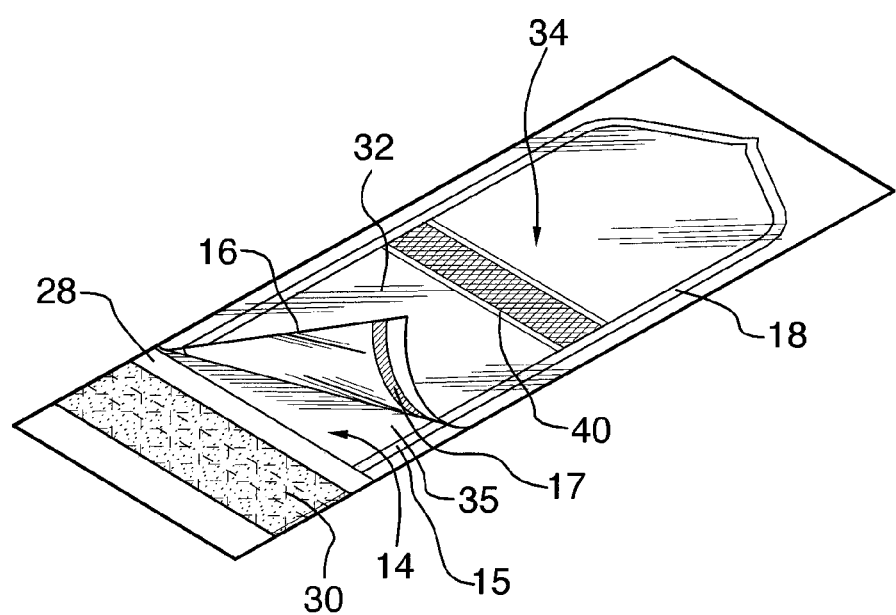
FIG. 2 is a perspective view of the pouch of FIG. 1 showing sheet material layers.

Referring to FIGS. 1 and 2, a pouch 10 is illustrated for use during a sterilization process and containment of sterilized surgical instruments 12 thereafter. After the surgical instruments 12 are sterilized, their sterility can be maintained for at least a year provided the pouch 10 is not damaged. The pouch 10 comprises a first sterilant permeable sheet material 14 and a sterilant impermeable sheet material 16, both of which are typically rectangular sheet material. The first sterilant permeable sheet material 14 is typically made from Kraft paper, which is permeable to sterilants such as steam, water vapor and sterilization gases, such as ethylene oxide. The sterilant impermeable sheet material 16 is typically made from a transparent polymer such as, for example, polyester, or a polyester/polyolefin laminate, that is impermeable to water vapor, steam and typical sterilizing gases. The sheet materials 14, 16 include respective first and second sealing strips 15, 17 which are typically heat sealed together along a portion thereof to provide a peripheral seal area 18 and which define the pouch 10 having an inner pouch volume 20. Several designs of peripheral seals are known to those skilled in the art and typically include one or more seal lines, which follow three sides of the rectangle.

Still referring to FIG. 1, an open pouch end 24 is located at one end of the pouch 26 and is used by an operator to locate the surgical instruments 12 to be sterilized inside the pouch volume 20. A sealing flap 28 extends away from the first sterilant permeable sheet material 14. The sealing flap 28 typically includes an adhesive strip 30 for sealing the flap 28 to an outer surface 32 of the sterilant impermeable sheet material 16. A number of sealing flap designs and methods of sealing the pouch are known to those skilled in the art One of the problems of currently used sterilization pouches is that a sterilization indicator material, typically in the form of an ink dot or ink strip, is either located exterior of the pouch 10, and therefore does not provide an accurate reading of when sterilization conditions have been met inside the sealed pouch volume 20, or inside the pouch volume behind a barrier. In the latter case, the barrier prevents the surgical instruments from damaging the ink dot, but disadvantageously the ink material may leak and pass through gaps in the barrier and contaminate the surgical instruments. Disadvantageously, when the indicator is printed on the porous paper, even if it is on the inner surface of the pouch, the indicator will change color even if the sterilant only reaches the exterior face of the paper.

Figure 3A:
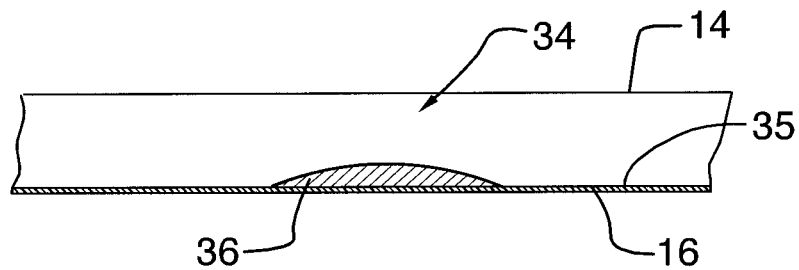
FIGS. 3A, 3B and 3C are cross sectional views taken along lines 3-3' of FIG. 1 showing three embodiments of a sterilization indicator.
Figure 3B:
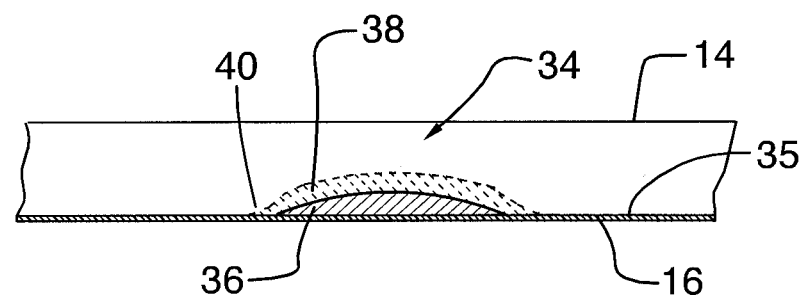

Referring to FIGS. 2, 3A, and 3B, our sterilization indicator 34 successfully addresses this problem. In one embodiment, the sterilization indicator 34 comprises a sterilization indicator material 36, which is typically an indicator ink strip (as illustrated in FIG. 2) or an ink dot, is located inside the pouch volume 20 and is printed on an inner surface 35 of the sterilant impermeable sheet material 16. The ink strip extends across the width of the pouch to the seal 18. In this embodiment, the sterilant first enters the pouch volume 20 via the first sterilant permeable sheet material 14 and then contacts the indicator material 36 causing it to change color. Also contemplated is a chip or sensor which may be used instead of an ink strip or ink dot, and which is able to detect time and temperature.

Figure 4:
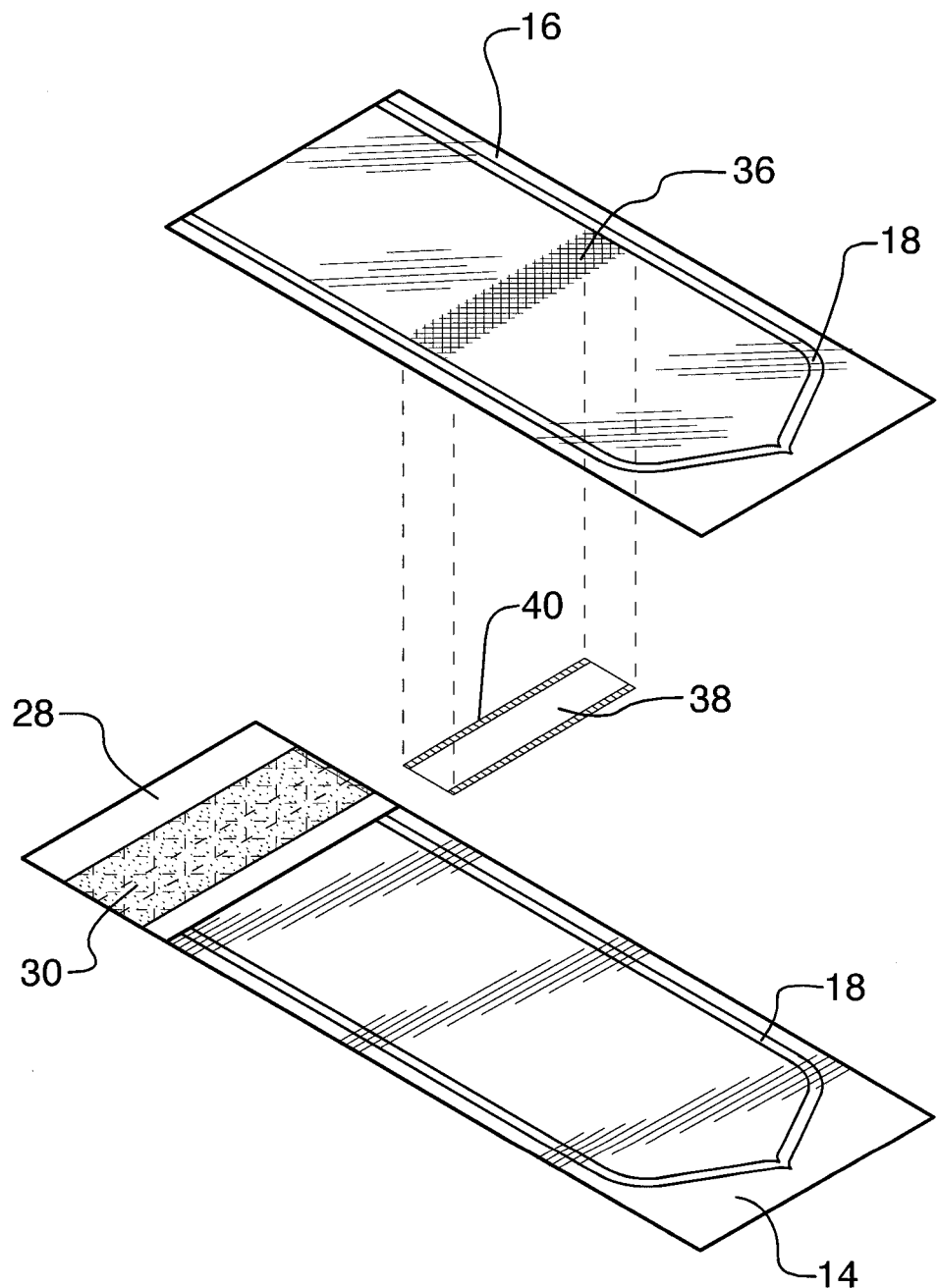
FIG. 4 is an exploded perspective view of a sterilization pouch showing an embodiment of a discrete strip sterilization indicator.

Referring to FIGS. 3B and 4, if required a second sterilant permeable sheet material 38 can located over the sterilization indicator material 36 and sandwiches the sterilization indicator material 36 with the inner surface 35 of the sterilant impermeable sheet material 16 so that during sterilization, the sterilant can permeate through the layer of material 38 and contact the indicator material 36 causing it to change color. In the example illustrated in FIGS. 3B and 4, the second sterilant permeable sheet material 38 is a strip. The second sterilant permeable material 38 is sufficiently permeable to allow any sterilant to pass therethrough, and yet does not permit the ink from the indicator material 36 to flow into the pouch volume 20. The sterilant can be any sterilant known to those skilled in the art, for example, a gas, such as ethylene oxide, steam, ozone, chemical vapor, x-ray ebeam, UV, HCFC, paracetic acid, dielectric barrier discharge (DBD) plasma and gliding arc (GA) plasma.

The location of the indicator material 36 behind the second sterilant permeable layer 38 also protects the indicator material 36 from damage during transit or during removal of the instruments 12 after sterilization once the pouch 10 is opened and the instruments 12 removed.

The location of the indicator material 36 inside the pouch 10 provides an accurate indication as to the sterilization processing conditions inside the pouch 10 that the instruments 12 are exposed to.

Still referring to FIGS. 3B and 4, the strip of second sterilant permeable sheet material 38 includes a peripheral area 40, which is sealed to the inner surface 35 of the sterilant impermeable sheet material 16 using, for example, heat sealing and forms a discrete indicator area. If desired additional ink dots can be used, especially in pouches having large dimensions and which can hold a number of surgical instruments. The sterilization indicator material 36 can be any shape, such as for example, a dot, a line, square, arrow-shaped. If desired, a company logo and even legible indicia may be formed of the indicator ink in lieu of the dot shape shown. The inks used to print the dot are well known in the art and are used to monitor sterilization exposure to such diverse sterilants as such as, for example, ethylene oxide, steam, ozone, chemical vapor, x-ray ebeam, UV, HCFC, paracetic acid, dielectric barrier discharge (DBD) plasma and gliding arc (GA) plasma, dry heat, ethylene oxide gas, formaldehyde gas, hydrogen peroxide gas, radiation and other inorganic and organic agents suitable for such purposes.

Indicators used herein are classified by their intended use and are described in detail in International Standard 15011140-1 (reference number ISO 11140-1:2005(E), entitled: Sterilization of health care products-Chemical indicators-Part 1: General requirements).

The indicators are classified into six groups, which are further subdivided by the sterilization process for which they are designed to be used. The classification structure used is solely to denote the characteristics and intended use of each type of indicators when used as defined by the manufacturer. Class 1 are process indicators that are intended for use with individual units (for example, packs, containers) to indicate that the unit has been directly exposed to the sterilization process and to distinguish between processed and unprocessed units. They are designed to react to one or more of the critical process variables. Class 2 are indicators for use in specific tests as defined in relevant sterilizer/sterilization standards. Class 3 are single variable indicators that are designed to react to one of the critical variables and are intended to indicate exposure to a sterilization process at a stated value of the chosen variable. Class 4 are multi-variable indicators that are designed to react to two or more of the critical variables and are intended to indicate exposure to a sterilization cycle at stated values of the chosen variables. Class 5 are integrating indicators that are designed to react to all critical variables. The stated values are generated to be equivalent to or to exceed the performance requirements given in ISO 11138 series for biological indicators. Class 6 are emulating indicators that are cycle verification indicators which are designed to react to all critical variables for specified sterilization cycles. The stated values are generated from the critical variables of the specified sterilization process. For the different sterilization processes, the following are defined as being critical variables:

Steam: Time, temperature and water (delivered by saturated steam)

Dry heat: Time and temperature

Ethylene oxide: Time, temperature, relative humidity and ethylene oxide concentration Irradiation: Total absorbed dose Steam-formaldehyde: Time, temperature, water (as delivered by saturated steam) and formaldehyde concentration Vapourised hydrogen peroxide: Time, temperature, hydrogen peroxide concentration and, if applicable, plasma.

Commercial indicator products that may be used include, but are not limited to, such products as NAMSA (distributed by Sun Chemical), Tempil Ink, and Steritec.

Use of inks giving a substantial color change on exposure to steam, water vapor, organic agent such as formaldehyde, radiation, or a gas such as ethylene oxide exposure and/or other agents mentioned are typically used.

Figure 3C:
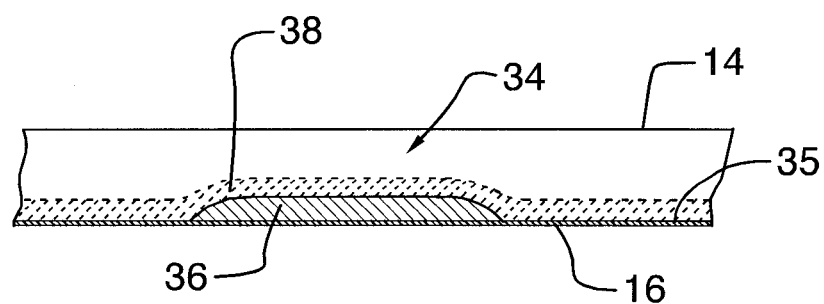
Figure 5:
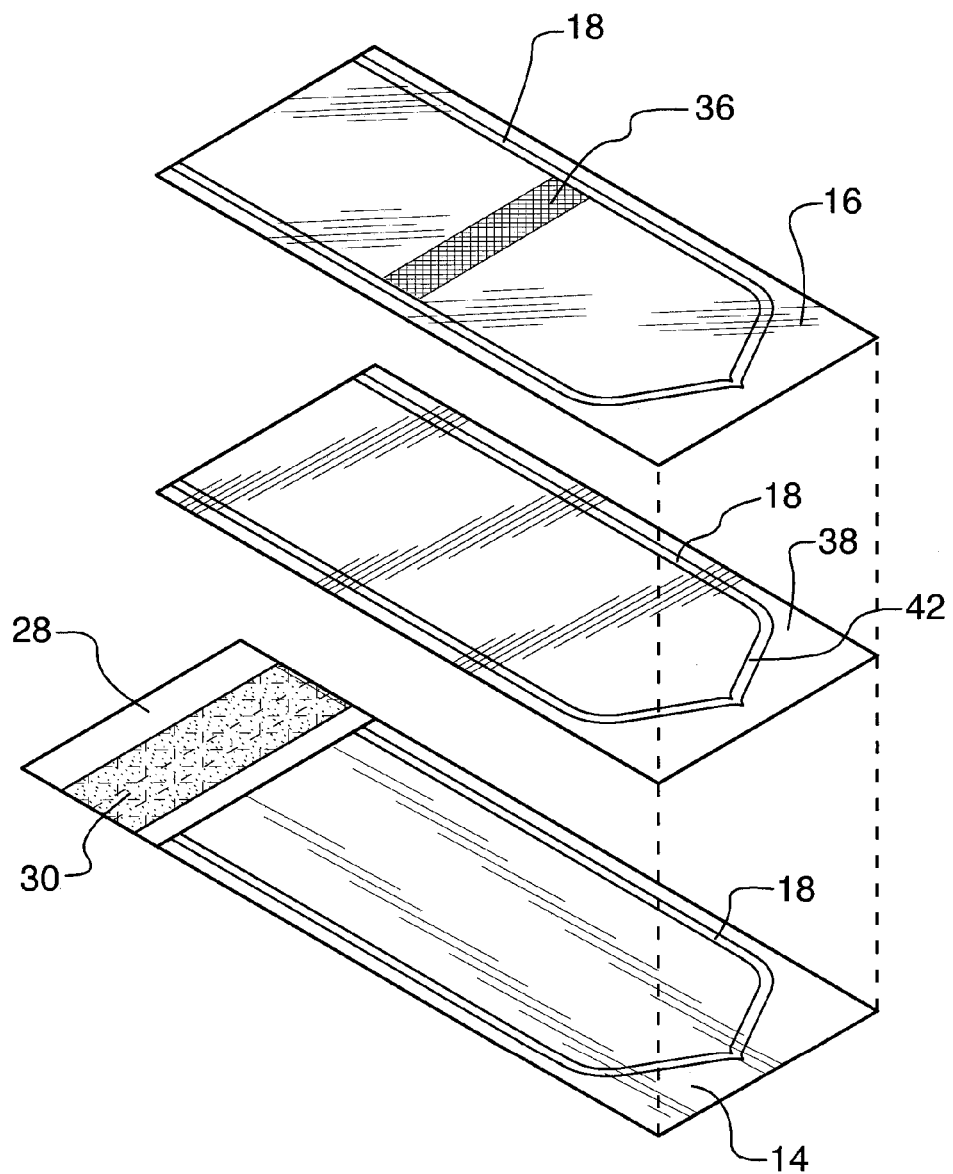
FIG. 5 is an exploded perspective view of a sterilization pouch showing an embodiment of a sterilization indicator sandwiched between a sterilant permeable sheet and a sterilant impermeable sheet.

Referring now to FIGS. 3C and 5, an alternative embodiment of the sterilization indicator 34 comprises the indicator material 36 printed on the inner surface 35 of the sterilant impermeable sheet material 16 and sandwiched between a rectangular second sterilant permeable sheet material 38 which includes a third sealing strip 42. The rectangular second sterilant permeable sheet material 38 lies against the indicator material 36 and is heat sealed to the first and second sealing strips 15, 17 along its peripheral area 40, thereby sandwiching the peripheral area 40 of the rectangular second sterilant sheet material 38 between the peripheral area 18 of the sheets 14, 16.

Figure 6:
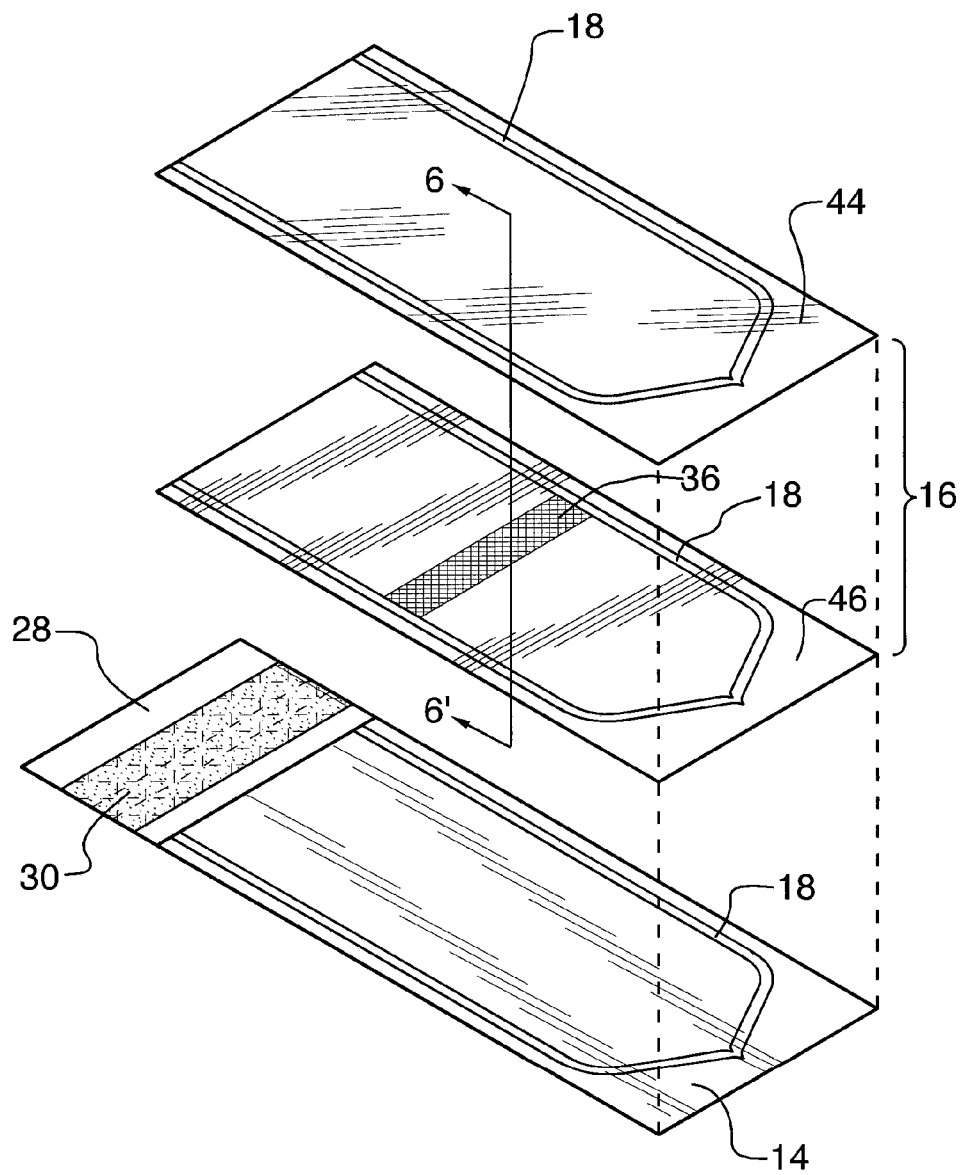
FIG. 6 is an exploded perspective view of a sterilization pouch showing the laminate layers of the sterilant impermeable sheet.
Figure 8A:
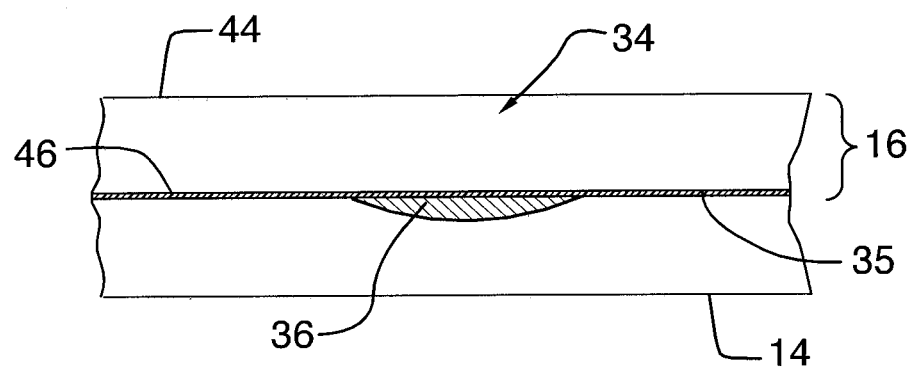
FIGS. 8A and 8B are cross sectional views taken along lines 6-6' and 7-7' of FIGS. 6 and 7 respectively.

As described above, the sterilant impermeable sheet material 16 comprises a laminate of two layers. One layer is a polyethylene sheet 44; the other layer is a polypropylene sheet 46. The sheets 44 and 46 are typically held together by adhesive. Referring now to FIGS. 6 and 8A an alternative embodiment of the sterilization indicator 34 comprises the indicator material 36 printed on the inner surface 35 of the polypropylene sheet 46, which faces the inside of the pouch volume 20.

Figure 7:
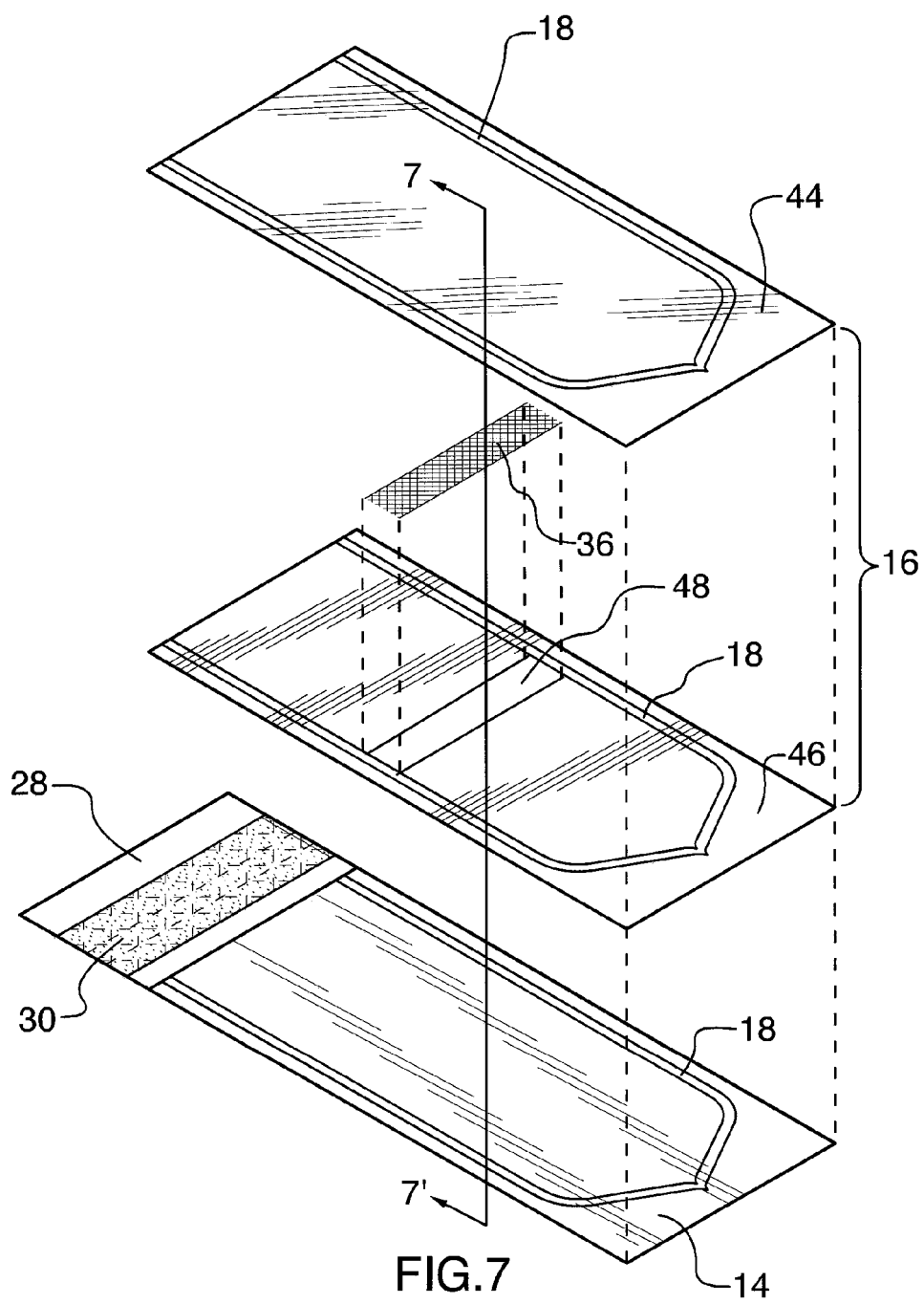
FIG. 7 is an exploded perspective view of a sterilization pouch showing the sterilization indicator sandwiched between the laminate layers.
Figure 8B:
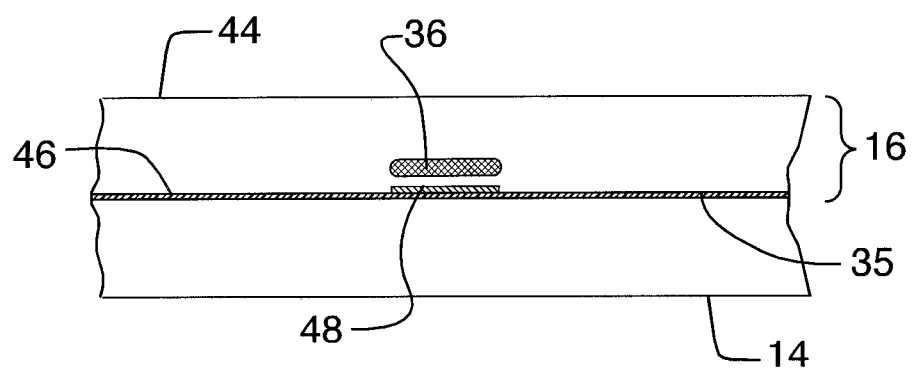

As best illustrated in FIGS. 7 and 8B, the indicator material 36 may also be sandwiched between the polypropylene sheet 46 and the polyethylene sheet 44. A sterilant permeable area 48 is located adjacent the indicator material 36 and is a portion of the polypropylene sheet 46 which is permeable to sterilant.

It should also be noted that the indicator material 36 may be printed on the inner surface of the sterilant permeable material 14 and sandwiched thereagainst by the second sterilant permeable material 38 using either the strip or the sheet of sterilant permeable material as described above.

Figure 9:
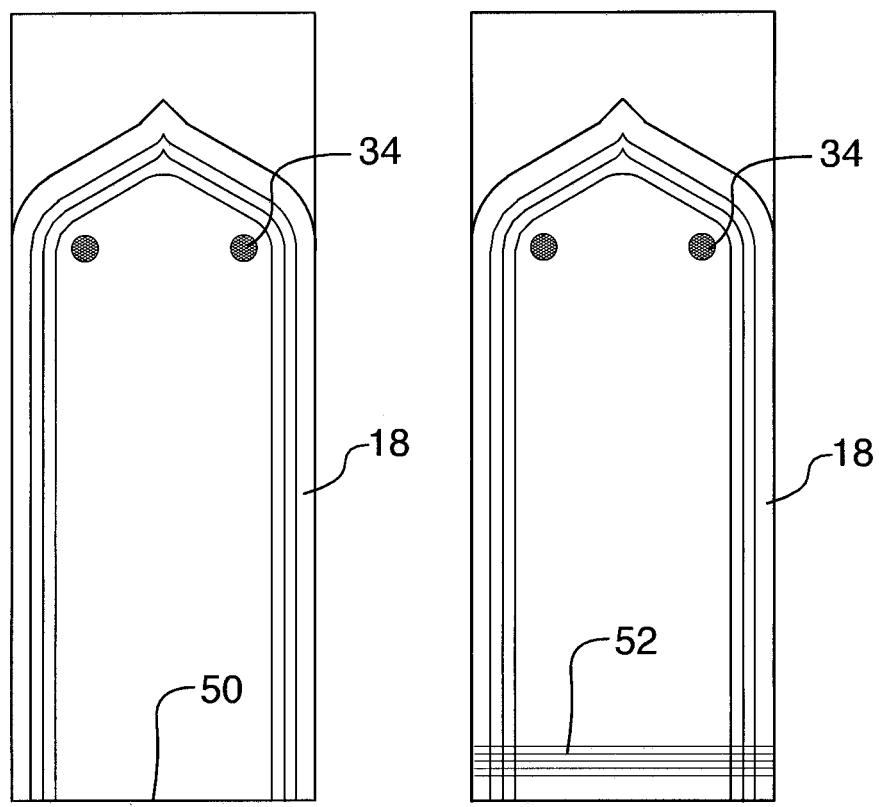
FIG. 9 is a top view of two sterilization pouches showing a pouch with an open end portion and a thermally sealed end portion.
Figure 10:
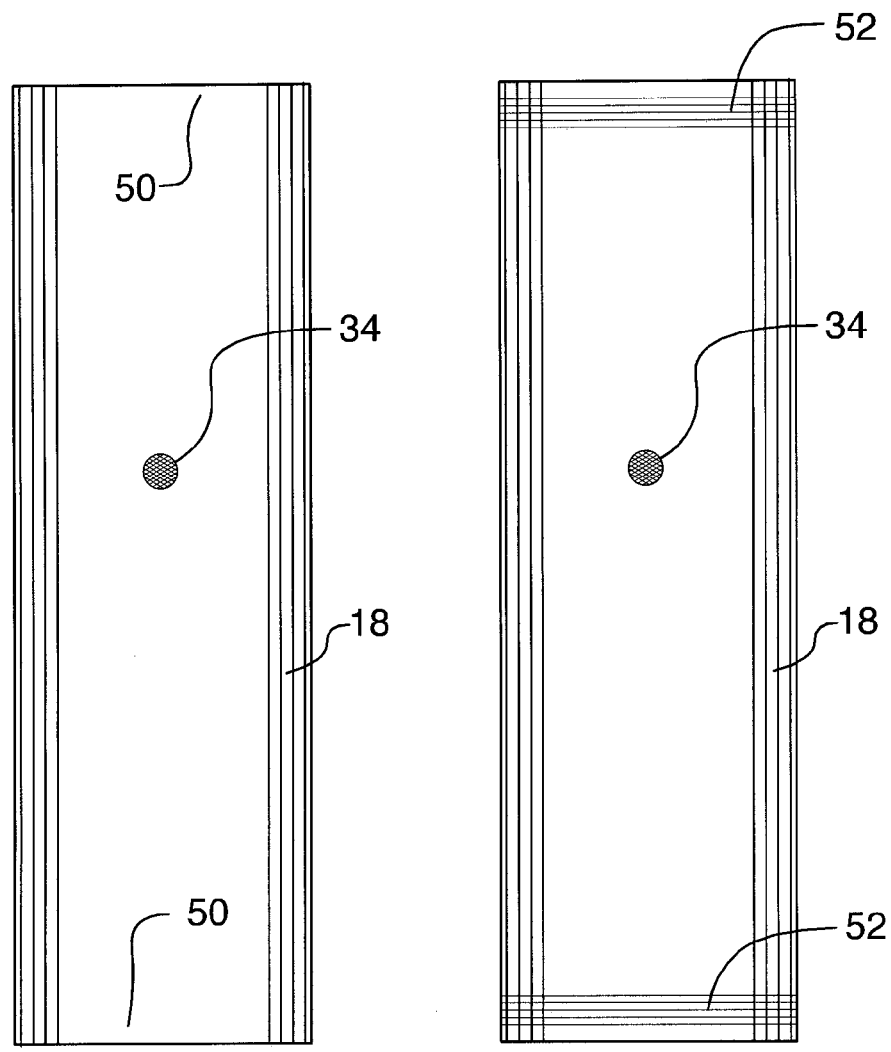
FIG. 10 is a top view of two sterilization pouches showing a pouch with two open end portions and two thermally sealed end portions Further details of the discovery and its advantages will be apparent from the detailed description included below.

Referring to FIGS. 9 and 10, an alternative seal may be used once the surgical instrument are located inside the pouch. FIG. 9 shows a pouch in which one sealable open end 50 can be thermally sealed by the user using, for example, a hand held thermal sealer to create a seal 52. FIG. 10 shows an alternative pouch in which an elongate strip of pouch is dispensed from a roll (not shown) and cut to a desired length to create two sealable open ends 50. As with the pouch shown in FIG. 9, the two sealable open ends 50 can be thermally sealed, after the surgical instruments are located inside the pouch, by the user using a hand held thermal sealer to create two seals 52 located at either end of the pouch.

Although the above description relates to a specific embodiment as presently contemplated by the inventor, it will be understood that the discovery in its broad aspect includes mechanical and functional equivalents of the elements described herein.

What is claimed is:

1. A sterilizable pouch for a surgical instrument, the pouch comprising:
    a first sterilant permeable sheet having a first sealing strip;
    a sterilant impermeable sheet having a second sealing strip, the first sealing strip being sealed to the second sealing strip to define the pouch, the pouch having at least one pouch volume configured to store the surgical instrument and at least one sealable open portion configured to seal the pouch after the surgical instrument is located inside the at least one pouch volume, wherein the sterilant impermeable sheet is a laminate, which laminate includes a polyethylene sheet and a polypropylene sheet, the polypropylene sheet facing inside the pouch; and
    an indicator material configured to indicate sterile processing conditions inside the pouch, the indicator material being located on an inner surface of the sterilant impermeable sheet inside the at least one pouch volume; and
    a second sterilant permeable sheet located over the indicator material so as to sandwich the indicator material between the polypropylene sheet and the second sterilant permeable sheet.

2. The pouch, according to claim 1, in which the indicator material is located on the inner surface of the polypropylene sheet facing the inside of the pouch.

3. The pouch, according to claim 1, in which the second sterilant permeable sheet is a strip, the strip extending across substantially the entire width of the pouch.

4. The pouch, according to claim 1, in which the second sterilant permeable sheet is a sheet which covers substantially all of the inner surface of the polypropylene sheet.

5. The pouch, according to claim 4, in which the sterilant permeable material sheet includes a third sealing strip sealed to the first and second sealing strips and sandwiched therebetween.

6. The pouch, according to claim 1, in which the indicator material is sandwiched between the polypropylene sheet and the polyethylene sheet, the polypropylene sheet having a sterilant permeable area located adjacent the indicator material.

7. The pouch, according to claim 6, in which the sterilant permeable area is a portion of the polypropylene material which is permeable to sterilant.

8. The pouch, according to claim 1, in which the indicator material is a chip or a sensor.

9. A sterilization indicator for use with a sterilizable pouch having a first sterilant permeable sheet and a sterilant impermeable sheet sealed together along a portion of a peripheral area to define the pouch, the pouch having at least one pouch volume configured to store the surgical instrument and at least one sealable open portion configured to seal the pouch after surgical instruments are located inside the at least one pouch volume, the sterilization indicator comprising:
    an indicator material configured to indicate sterile processing conditions inside the pouch, the indicator material being located on an inner surface of either of the first sterilant permeable sheet or the sterilant impermeable sheet inside the at least one pouch volume; and
    a layer of sterilant permeable material located over the indicator material to sandwich the indicator material between the layer of sterilant permeable material and the inner surface of either of the first sterilant permeable sheet or the sterilant impermeable sheet, the layer of sterilant permeable material being sealed around the indicator material.

10. The sterilization indicator, according to claim 9, in which the layer of sterilant permeable material is sealed to the inner surface of the first sterilant permeable sheet or the sterilant impermeable sheet to cover the indicator material.

11. The sterilization indicator, according to claim 9, in which the layer of sterilant permeable material is sealed along its periphery to the inner surface of the first sterilant permeable sheet or the sterilant impermeable sheet to define a discrete indicator area.

12. The sterilization indicator, according to claim 11, in which the layer of sterilant permeable material is a strip of sterilant permeable material.

13. The sterilization indicator, according to claim 9, in which the layer of sterilant permeable material is a sheet of sterilant permeable material which covers substantially all of the inner surface of the first sterilant permeable sheet or the sterilant impermeable sheet.

14. The sterilization indicator, according to claim 13, in which the sterilant permeable material is sealed along the peripheral area together with the first sterilant permeable sheet or the sterilant impermeable sheet.

15. The sterilization indicator, according to claim 9, in which the indicator material is an ink dot.

16. The sterilization indicator, according to claim 9, in which the indicator material is an ink strip.

17. The sterilization indicator, according to claim 9, wherein the indicator material is a chip or a sensor.

18. A sterilizable pouch for a surgical instrument, the pouch comprising:
    a first sterilant permeable sheet and a sterilant impermeable sheet sealed together along a portion of a peripheral area to define the pouch, the pouch having at least one pouch volume configured to store the surgical instrument and at least one sealable open portion configured to seal the pouch after the surgical instrument is located inside the at least one pouch volume;
    an indicator material configured to indicate sterile processing conditions inside the pouch, the indicator material being located on an inner surface of either the first sterilant permeable sheet or the sterilant impermeable sheet inside the at least one pouch volume; and a layer of sterilant permeable material located over the indicator material to sandwich the indicator material between the layer of sterilant permeable material and the inner surface of either of the first sterilant permeable sheet or the sterilant impermeable sheet, the layer of sterilant permeable material being sealed around the indicator material.

19. The pouch, according to claim 18, in which the layer of sterilant permeable material is sealed to the inner surface of the first sterilant permeable sheet or the sterilant impermeable sheet to cover the indicator material.

20. The pouch, according to claim 18, in which the layer of sterilant permeable material is sealed along its periphery to the inner surface of the first sterilant permeable sheet or the sterilant impermeable sheet to define a discrete indicator area.

21. The pouch, according to claim 20, in which the layer of sterilant permeable material is a strip of sterilant permeable material.

22. The pouch, according to claim 18, in which the layer of sterilant permeable material is a sheet of sterilant permeable material which covers substantially all of the inner surface of the first sterilant permeable sheet or the sterilant impermeable sheet.

23. The pouch, according to claim 22, in which the sterilant permeable material is sealed along the peripheral area together with the first sterilant permeable sheet or the sterilant impermeable sheet.

24. The pouch, according to claim 18, in which the indicator material is an ink dot.

25. The pouch, according to claim 18, in which the indicator material is an ink strip.

26. The pouch, according to claim 18, in which the indicator material is a chip or a sensor.

27. The pouch or the sterilization indicator, according to claim 1, in which the indicator material is a Class 1, Class 2, Class 3, Class 4, Class 5 or Class 6 indicator as defined by International Standard ISO 11140-1.

28. The pouch or the sterilization indicator, according to claim 1, in which the indicator material is reactive to one or more sterilants selected from steam, dry heat, irradiation, ethylene oxide, steam-formaldehyde, or vapourized hydrogen peroxide, ozone, HCFC, paracetic acid, dielectric barrier discharge (DBD) plasma or gliding arc (GA) plasma.

* * * * *